(12) United States Patent
Zhang et al.

(10) Patent No.: US 6,780,650 B2
(45) Date of Patent: Aug. 24, 2004

(54) LIGAND BINDING ASSAYS FOR VANILLOID RECEPTORS

(75) Inventors: Sui-Po Zhang, Bala Cynwyd, PA (US); Ellen E. Codd, Blue Bell, PA (US)

(73) Assignee: Ortho-McNeil Pharmaceutical, Inc., Raritan, NJ (US)

( * ) Notice: Subject to any disclaimer, the term of this patent is extended or adjusted under 35 U.S.C. 154(b) by 109 days.

(21) Appl. No.: 09/975,650

(22) Filed: Oct. 11, 2001

(65) Prior Publication Data

US 2002/0115105 A1 Aug. 22, 2002

Related U.S. Application Data

(60) Provisional application No. 60/240,628, filed on Oct. 15, 2000.

(51) Int. Cl.[7] ...................... G01N 30/566; G01N 33/567
(52) U.S. Cl. ....................................... 436/501; 435/7.21
(58) Field of Search ......................... 435/7.1, 7.2, 7.21; 436/501

(56) References Cited

FOREIGN PATENT DOCUMENTS

| WO | WO 99/09140 A1 | 2/1999 |
|---|---|---|
| WO | WO 00/29577 A1 | 5/2000 |

OTHER PUBLICATIONS

Acs, G., et al, "{3H} Resiniferatoxin binding by the human vanilloid (capsaicin) recepor", Molecular Brain Research 1994 23:185–190.
Bevan, S., et al, "Sensory neuron–specific actions of capsaicin: mechanisms and applications," Trends Pharmacolo. Sci. 1990 11:330–333.
Bevan, S., et al., "Capsazepine: a competitive antagonist of the sensory neuron excitant capsaicin," British Journal Pharmacolo. 1992 107:544–552.
Caterina, M. J., et al. "The capsaicin receptor: a heat–activated ion channel in the pain pathway," Nature 1997 389:816–824.
Szallasi, A., et al., "Specific binding of resiniferatoxin, an ultrapotent capsaicin analog, by dorsat root ganglion membranes," Brain Research 1990 524:106–111.
Szallasi, A., et al., "{3H} resiniferatoxin binding by the vanilloid receptor: species–related differences, effects of temperature and sulfhydryl reagents," Naunyn–Schmiedeberg's Archives of Phamacology, 1993 347:84–91.
Szallasi, A., et al., "Proton inhibition of {3H} resiniferatoxin binding to vanilloid (capsaicin) receptors in rat spinal cord," Molecular Pharmacology 1995 289:181–187.
Szallasi, A., et al., "Characterization by {3H} resiniferatoxin binding of a human vanilloid (capsaicin) receptor in post–mortem spinal cord," Neuroscience Letters 1994 165:101–104.
Szallasi, A., et al., "Competitive inhibition by capsazepine of {3H} resiniferatoxin binding to central (spinal cord and dorsal root ganglia) and Peripheral (urinary bladder and Airways) vanilloid (capsaicin) receptors in the Rat," Journal Pharmacol. Exp. Ther. 1993 267:728–33.
Szallasi, A., et al., "Vanilloid (capsaicin) receptors in the rat: distribution in the brain, regional differences in the spinal cord, axonal transport to the periphery, and depletion by systemic vanilloid treatment," Brain Research 1995 703:175–183.
Szolcsanyi, J., "Capsaicin–sensitive sensory nerve terminals with local and systemic efferent functions: facts and scopes of an unorthodox neuroregulatory mechanism," Progress in Brain Research 1996 113:343–359.
Szolcsanyi, J., "Actions of capsaicin on sensory receptors," Capsaicin in the study of pain 1993 J.N. Wood, ed.: Academic, London, UK pp. 1–26.
Szolcsanyi, J., et al., "Resiniferatoxin: an ultrapotent neurotoxin of capsaicin–sensitive primary afferent neurons," Annual N.Y. Academy of Sciences, 1991 632:473–475.
Tominaga, M., et al., "The cloned capsaicin receptor integrates multiple pain–producing stimuli," Neuron 1998 21:531–543.
Wood, J.N., et al., "Capsaicin–induced ion fluxes in dorsal root ganglion cells in culture," Journal of Neuroscience 1988 8:3208–3220.
Genbank Accession#NM_018727, Homo Sapiens Vanilloid receptor subtype 1 (VRI), MRNA.
PCT Search Report of PCT/US 01/42602 dated Mar. 11, 2002.

*Primary Examiner*—John D. Ulm

(57) ABSTRACT

The present invention describes an assay in which pH alters RTX affinity to VR1 receptors. The RTX affinity was increased with increasing pH from 4.1 to 8.6. Both the RTX affinity and apparent number of RTX binding sites were decreased with increasing pH from 8.6 to 10.6. The high pH may be causing the cell membranes to denature. These pH conditions (pH 8.0 to pH 9.0) provide a high signal to noise ratio, give a more robust assay and require use of less experimental materials.

14 Claims, 6 Drawing Sheets

Effect of pH on [$^3$H]RTX Binding to hVR1 Receptor

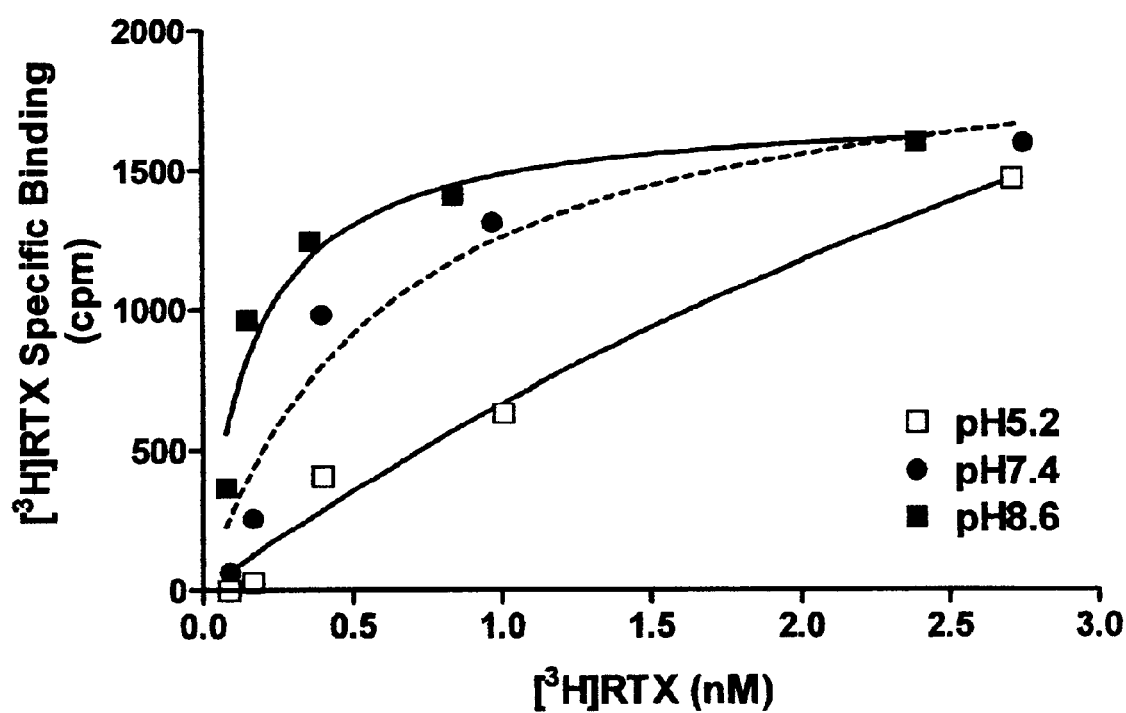
FIUGRE 2A

LIGAND BINDING ASSAYS FOR VANILLOID RECEPTORS

This application claims priority from U.S. Provisional Patent Application 60/240,628 filed Oct. 15, 2000 and entitled "Improved Ligand Binding Assays for Vanilloid Receptors.

BACKGROUND OF THE INVENTION

Noxious chemical, thermal and mechanical stimuli excite peripheral nerve endings of small diameter sensory neurons (nociceptors) in sensory ganglia (eg., dorsal root, nodose and trigeminal ganglia) and initiate signals that are perceived as pain. These neurons are crucial for the detection of harmful or potentially harmful stimuli (for example heat), tissue damage caused by local tissue acidosis, and physical movement (for example tissue stretch) that arise from changes in the extracellular space during inflammatory or ischaemic conditions (Wall and Melzack, 1994).

Capsaicin (8-methyl-N-vanillyl-6-nonenamide), the main pungent ingredient in "hot" capsicum peppers, and its analogs interact at specific membrane recognition sites called vanilloid receptors. These receptors are expressed almost exclusively by primary sensory neurons involved in nociception and neurogenic inflammation (Bevan and Szolcsanyi, 1990). Capsaicin is a very selective activator of thinly or unmyelinated nociceptive afferents (Szolcsanyi, 1993; Szolcsanyi, 1996). Capsaicin can be blocked by a selective antagonist, capsazepine. Another ligand is the potent tricyclic diterpene resiniferatoxin (RTX), (Szolcsanyi et al., 1991), a molecule that binds with nanomolar affinity at the capsaicin-binding site.

Recently, one receptor for capsaicin (VR1) was cloned from rat (Caterina et al., 1997) and shown to be a coincidence detector for H+ (low pH) and heat (Tominaga et al., 1998). VR1 is expressed in small nociceptive neurons of the dorsal root ganglion, consistent with its role in modulating peripheral pain (Tominaga et al., 1998). VR1 is a ligand-gated non-selective cation channel that shows pronounced outward rectification (Caterina et al., 1997). The vanilloid ("capsaicin") receptor VR1 is activated by capsaicin and RTX, and activation of VR1 is blocked by the antagonists capsazepine (CPZ); (Bevan et al., 1992) and ruthenium red (RR; (Wood et al., 1988)). Recently, rat VR1 and VR2 and a partial cDNA sequence of human sequences were disclosed in the WIPO publication WO 99/09140.

The densities of VR1 receptors can be tested using a [$^3$H]RTX binding assay (Szallasi and Blumberg, 1990; Szallasi and Blumberg, 1993). Indeed, high expression of VR1 receptors was observed in rat and human spinal cord and dorsal root ganglia (Szallasi et al, 1993; Szallasi and Goso, 1994; Acs et al., 1994). Protons inhibited [$^3$H]RTX binding to VR1 receptors (Szallasi et al. 1995).

Prior ligand binding assays using the VR-1 receptor teach that the pH must be near physiological conditions. In these assays, ligand binding was reduced by 50% and 70% at pH 8.0 and pH 9.0, respectively (Szallasi and Blumberg, 1993).

SUMMARY OF THE INVENTION

In contrast to what is suggested in the art, the present invention provides the surprising discovery that the binding capacity of certain ligands of the Vanilloid receptor increases at pH values that are greater than pH 7.4. The present invention provides improved assays to measure competitive vanilloid receptor binding of a known radiolabeled ligand and a test compound binding in aqueous buffers at a pH in the range of about 7.5–10.0. The present invention also provides the discovery that divalent cations also increase the binding capacity of certain ligands for the Vanilloid receptor. Therefore the aqueous solutions used for the methods of the present invention advantageously may include, as one component, a divalent cation.

The methods of the present invention are useful to find compounds that bind to Vanilloid receptors.

BRIEF DESCRIPTION OF THE DRAWINGS

FIG. 2. pH changes affinity of [$^3$H]RTX for the hVR1 receptor. FIG. 2A: Cell membranes (60 μg protein/ml) were incubated with varying concentrations of [$^3$H]RTX in buffer samples with differing pH at 25° C. for 60 min. (pH 5.2, pH 7.4 and pH 8.6)

DETAILED DESCRIPTION OF THE INVENTION

Figure 1:
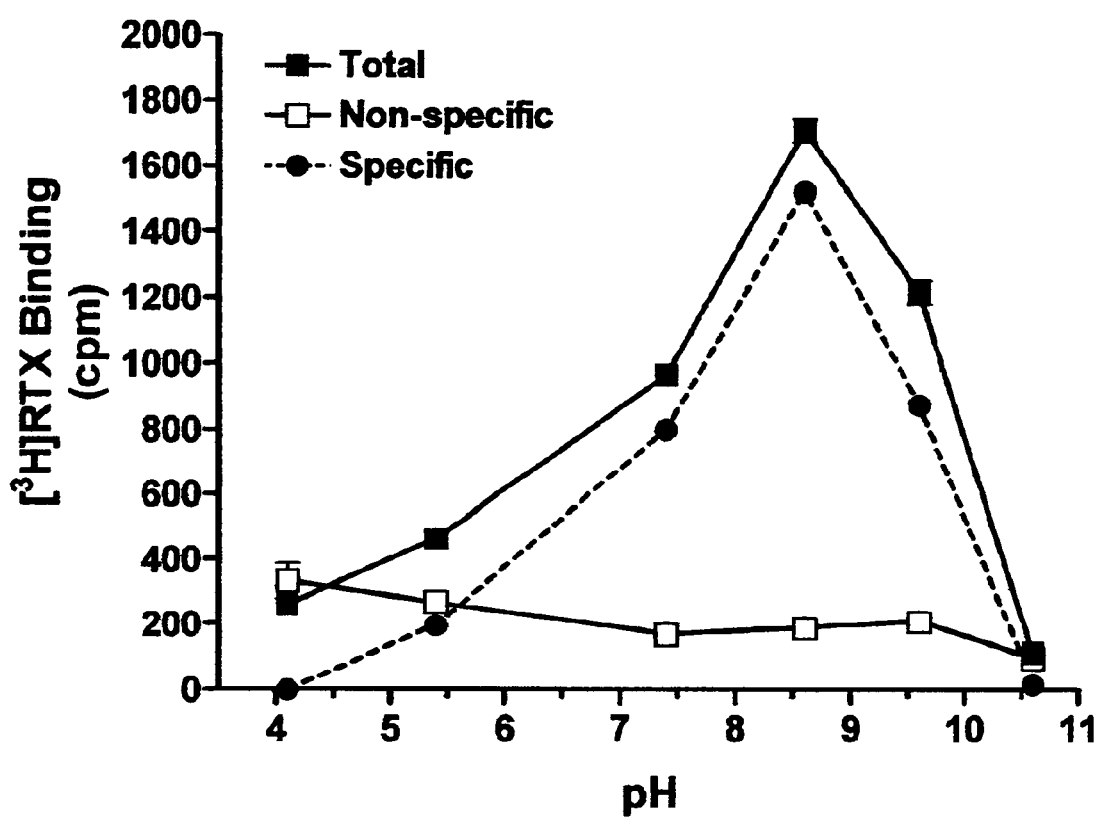
FIG. 1. Effect of pH on [$^3$H]RTX binding to the hVR1 receptor. Cell membranes (60 μg protein/ml) were incubated with [$^3$H]RTX (0.4 nM) in buffer samples with differing pH at 25° C. for 60 min. The results are representative of two experiments with each point assayed in triplicate.

Capsaicin is a compound of the formula:

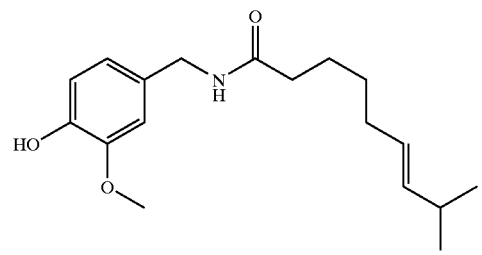

Capsazepine is a compound of the formula:

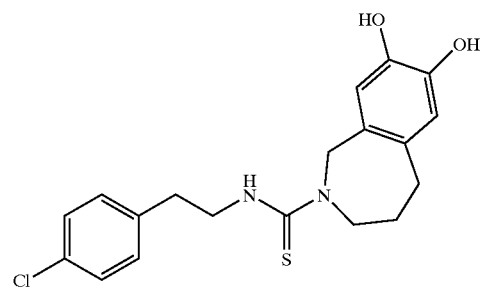

Resiniferatoxin is a compound of the formula:

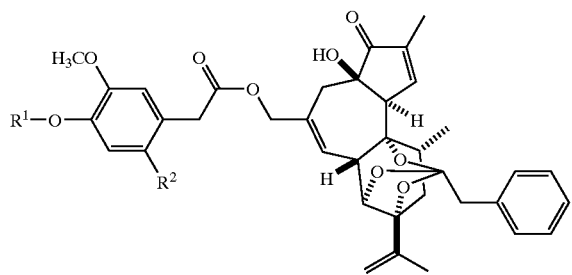

The present invention provides improved assays to measure compound binding to a vanilloid receptor comprising the steps,
(a) forming, in an aqueous solution having a pH in the range of about 7.5 to about 10.0, a liquid composition comprising a test compound, a labeled ligand, and at least a ligand-interacting portion of a vanilloid receptor protein;
(b) incubating the solution for a time sufficient to permit the test compound and labeled ligand to contact the vanilloid receptor;
(c) measuring the amount of labeled ligand bound to the protein; and
(d) determining if the test compound bound to the receptor by observing a reduction in the amount of expected labeled ligand.

The methods can optionally include a stop of removing unbound labeled ligand from the solution and also optionally the step of isolating the receptor protein.

The aqueous solution of the present invention may be composed of any buffering species that provides a suitable pH. The choice of a buffer to provide suitable pH is well known in the art. The pH suitable for the methods of the present invention are in the range of about 7.5 to about 10.0, preferably from about pH 8.0 to about 9.5, more preferably from about pH 8.1 to about 9.1, and particularly at about pH 8.6.

There are a variety of buffers well known in the art that can be used for the methods of this invention. A preferred buffer is HEPES (N-[2-hydroxyethyl]piperazine-N'-2-ethanesulfonic acid with a pka of about 7.55. Other buffers include, but are not limited to MES (morpholinoethane sulfonic acid, pka about 6.2); MOPS (morpholinopropane sulfonic acid, pka about 7.2); PIPES (Piperazine-N,N'-bis (2-ethane sulfonic acid, pka about 6.8); and TES (N-Tris (hydroxymethyl)methyl-2-aminoethane sulfonic acid, pka about 7.5).

The solution may contain agents that minimize protein adsorption onto the surface of the vessel containing the solution. Such agents are well know and include for example, a protein such as bovine serum albumin or immunoglobulin, or an amino acid, such as glycine.

Advantageously, the solution may contain a divalent cation. Use of a divalent cation has been demonstrated here to enhance ligand interaction with the vanilloid receptor. Particularly preferred divalent cations are Magnesium and Calcium. Other divalent cations can be tested and used in these assays without undue experimentation. Divalent cations are preferably used at a concentration in the range of about 0.1 mM to about 10 mM. Agents that chelate divalent cations, such as EDTA or EGTA, are preferably not used in the aqueous solution.

The term "test compound" is used herein to refer to a candidate molecule having the potential capacity to interfere with the binding of a labeled ligand and the ligand-interacting portion of a vanilloid receptor.

The term "labeled ligand" as used herein in connection with the assays of this invention is a ligand known to bind to the vanilloid receptor protein, which has a detectable label including, but not limited to, a fluorescent molecule or a radioactive tag. Examples of fluorescent molecules suitable for use in the present invention include, but are not limited to, coumarins, xanthene dyes such as fluoresceines, rhodols, and rhodamines, resorufins, cyanine dyes bimanes, acridines, isoindols, dansyl dyes, aminophthalic hydrazides such as luminol and isoluminol derivatives, aminophthalimides, aminonapthalimides, aminobenzofurans, aminoquinolines, dicanohydroquinones, and europium and terbium complexes and related compounds. The types of radioactive tags used to label the ligand include any of a variety of known $\beta$-particle emitters or Auger electrons, including [$^3$H], [$^{14}$C], [$^{35}$S], [$^{33}$P], [$^{32}$P], [$^{125}$I], and [$^{131}$I], with [$^3$H] being generally preferred due to its relative safety. In a most preferred embodiment of the present invention, the concentration of labeled ligand used is closely matched to the natural ligand's affinity (Kd) for its receptor. A preferred labeled ligand is resiniferatoxin or RTX, of which tritiated forms are well known.

The term "ligand-interacting portion of a vanilloid receptor protein" refers to that region(s) of a vanilloid receptor protein that interacts with the ligand being used in the assay. Proteins are typically divided into functional regions including transmembrane regions, one or more binding domains, intracellular regions, extracellular regions, regions that include particular folding characteristics and the like. Those of ordinary skill in the art are able to create truncated fragments, receptor protein with altered sequences and chimeric proteins that can be used to define these functional regions. In this case it is contemplated that the assay incorporate at least that portion of the vanilloid receptor that binds to the ligand used in the assay.

Vanilloid receptors suitable for the methods of the present invention include receptors derived from any mammal, particularly human, mouse, rat, and monkey. There are several distinct genes that encode different vanilloid receptor proteins. A number of those are referenced in the publications cited herein. The preferred vanilloid receptors include those that bind resiniferatoxin including, but not limited to, VR-1. The VR-1 receptor may be obtained using methods well known in the art including using the human VR-1 sequence (as provided as GenBank accession number NM_018727).

The vanilloid receptors can be obtained from a number of sources. In one example, the vanilloid receptors are isolated from native cells, for example, but not limited to, dorsal root ganglia expressing the vanilloid receptors such as described by Szallasi and Blumberg, 1993. In another embodiment the vanilloid receptors are obtained from cells expressing a cDNA encoding a recombinant vanilloid receptor. Preferably, at least the ligand-interacting portion of the vanilloid receptor protein is used. However, the entire protein may be used or the ligand-interacting portion of the receptor protein may be combined with other portions of other proteins, for example, one or more membrane-binding domains from other proteins. These chimeric protein still retain vanilloid receptor protein ligand-binding characteristics.

Following the formation of the aqueous solution of step (a), the solution is incubated for a time sufficient to allow the ligand and the vanilloid receptor or the test compound and the vanilloid receptor to come into contact. Methods for determining a suitable incubation time can be determined using the examples as described herein.

Next, in a preferred embodiment, unbound labeled ligand is removed from the solution. Methods for removing unbound labeled ligand from the solution can be performed using any of a variety of techniques known in the art, such as suitable adsorption strategies, membrane separation techniques where the vanilloid receptor protein is membrane bound or through the use of molecules such as alpha 1 acid glycoprotein, and the like.

In a further step of the assay of this invention, the receptor protein is isolated from the aqueous solution. In one embodiment, the ligand binding domain of the vanilloid receptor protein is associated with a membrane, such as cellular membrane or artificial membrane preparations. In another embodiment, the vanilloid receptor is created as a soluble protein. Methods for removing membrane or isolating receptor protein are known in the art and include, for example, selective centrifugation methods, adsorption steps, column chromatography, antibody-mediated precipitation, and the like.

Preferably the methods of the assay of this invention are performed in order, however, those of ordinary skill in the art will understand that, as one example, the removing step and the isolating step may be combined as one step or performed in any suitable order that facilitates removal of unbound label from labeled receptor protein. Thus, in one assay the removing step may be performed before the isolating step, while in another assay, the format of the assay may be better performed if the isolating step and removing step are combined as a single step.

As a final step in the assay of this invention, suitable calculations and comparisons are made, using the appropriate controls, and the like to determine whether or not the test compound has bound to the ligand-interacting portion of the vanilloid receptor. In a preferred example, suitable controls are included in the assay that do not include test compound and permit a comparison between controls that do not include test compound and samples including test compound. A reduction in the amount of expected labeled ligand is indicative of test compound binding.

In a preferred assay of this invention, the ligand-interacting portion of the vanilloid receptor protein is associated with cell membrane and the isolating the receptor protein step comprises removing membrane from the aqueous solution.

The invention can be better understood by way of the following examples. These examples are representative of the preferred embodiments, but are not to be construed as limiting the scope of the invention.

EXAMPLE 1

Materials

Resiniferatoxin, capsaicin and capsazepine were purchased from Research Biochemical International (Natick, Mass.). HEPES and CASPO were purchased from Sigma (St. Louis, Mo.). [$^3$H]resiniferatoxin (RTX) was purchased from NEN (Boston, Mass.). HEK 293 cells were transfected with the human vanilloid receptor (VR1).

Methods

Cell culture. HEK 293 cells were grown as monolayers in DMEM (GIBCO) containing 10% fetal bovine serum and 1×PSA (Cascade Biologics) in an incubator with an atmosphere of 5% $CO_2$ at 37° C. HEK 293-hVR1 cells were grown in the same media containing 200 µg/ml of zeocin (Invitrogen).

Membrane preparation. Cells were washed with Hank's Balanced Salt Solution, dissociated with cell dissociation buffer (Sigma), and then centrifuged at 1000×g for 5 min. Cell pellets were homogenized in cold 20 mM HEPES buffer, pH 7.4, containing 5.8 mM NaCl, 320 mM sucrose, 2 mM $MgCl_2$, 0.75 $CaCl_2$ and 5 mM KCl and centrifuged at 1000× g for 15 min. The resultant supernate was then centrifuged at 4000× g for 15 min. The pelleted membranes were kept in a −80° C. freezer.

[$^3$H]RTX binding assay. The assay procedure was modified from that described previously (Szallasi and Blumberg, 1993). About 120 µg protein/ml from membranes were incubated with indicated concentrations of [$^3$H]RTX in 0.5 ml of the HEPES buffer (pH 4.1 to pH 8.6) or CASPO buffer (pH 8.6 to pH 10.6) containing 0.25 mg/ml fatty acid-free bovine serum albumin at 37° C. for 60 min. The reaction mixture was then cooled to 4° C., and 0.1 mg $α_1$-acid glycoprotein was added to each sample and incubated at 4° C. for 15 min. The samples were centrifuged at 18500× g for 15 min. The tip of the microcentrifuge tube containing the pellet was cut off. Non-specific binding was tested in the presence of 200 nM unlabeled RTX. Bound radioactivity was quantified by scintillation counting.

Results

Effect of pH on [$^3$H]RTX binding to hVR1 receptors. Protons are known to stimulate calcium influx via the VR1 receptor. To study whether protons affect [$^3$H]RTX binding, membranes were incubated with [$^3$H]RTX at various pH values from 4.2 to 10.6. The results showed a biphasic effect (FIG. 1). [$^3$H]RTX binding increased from pH 4.2 to pH 8.6, but decreased from pH 8.6 to pH 10.6. The non-specific binding did not change significantly.

Figure 2B:
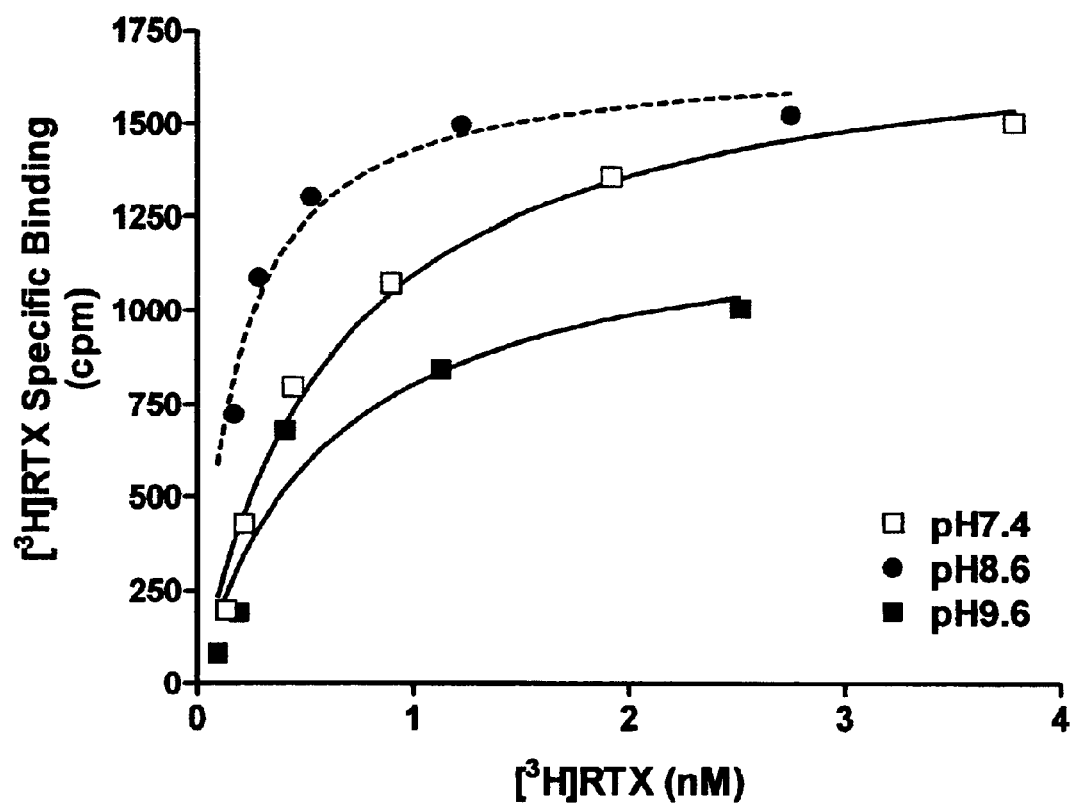
FIG. 2B: Cell membranes (60 μg protein/ml) were incubated with varying concentrations of [$^3$H]RTX in buffer samples with differing pH at 25° C. for 60 min. (pH 7.4, pH 8.6 and pH 9.6).

Mechanisms of pH affecting [$^3$H]RTX binding. To investigate whether the pH changes observed resulted from changes in the binding affinity or the apparent density of the binding sites, we performed saturation binding of [$^3$H]RTX at pH 5.2, pH 7.4, pH 8.6 and pH 9.6 (FIG. 2). The data are representative of two experiments with each point assayed in duplicate. The results demonstrated that the affinity ($K_d$ values) of [$^3$H]RTX for hVR1 receptors was increased with increasing pH from 5.2 to 8.6 without a change in the number of binding sites ($B_{max}$), whereas the affinity was decreased with increasing pH from 8.6 to 9.6 with a decrease in number of binding sites.

The $K_d$ values of [$^3$H]RTX and the $B_{max}$ values are summarized in Table Table 1.

TABLE 1

$K_d$ and $B_{max}$ values of [$^3$H]RTX binding to hVR1 receptor in buffers with different pH value.

| pH | $K_d$ (nM) | $B_{max}$ (fmol/mg protein) |
|---|---|---|
| pH 5.1 | 6.62 ± 5.58 | ND |
| pH 7.4 | 0.65 ± 0.12 | 928 ± 53 |
| pH 8.6 | 0.18 ± 0.04 | 869 ± 41 |
| pH 9.6 | 0.60 ± 0.31 | 661 ± 127 |

$K_d$ and $B_{max}$ values were obtained from FIG. 2. ND: not determinable.

Figure 3A:
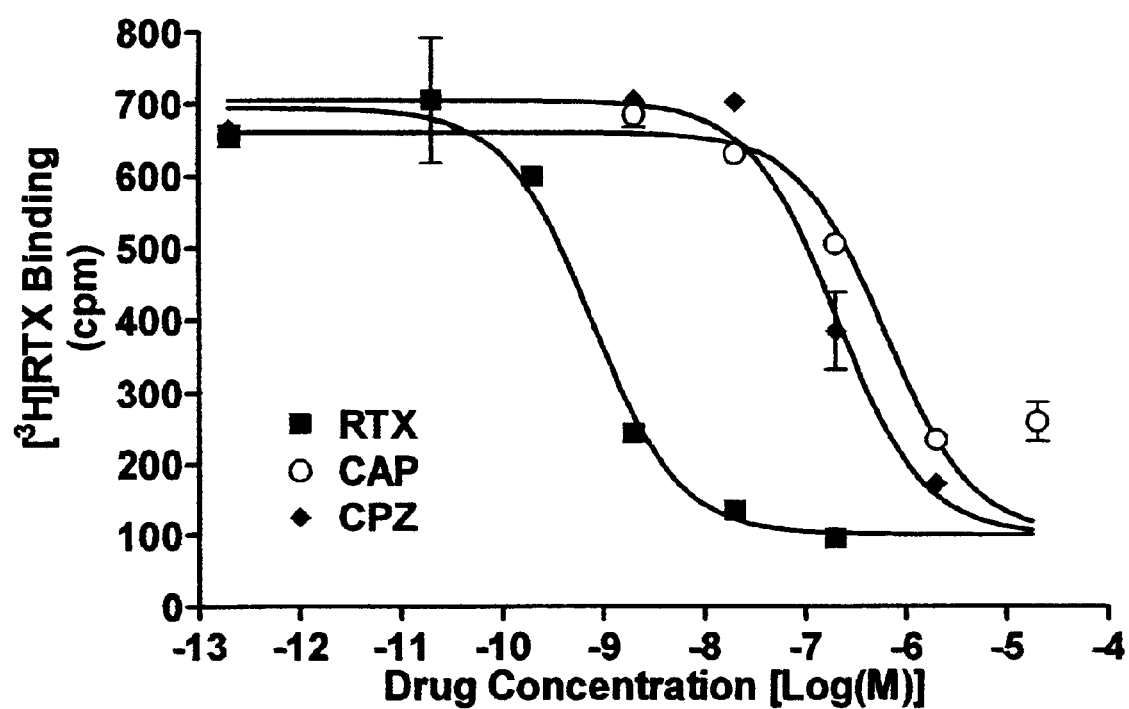
FIG. 3. Effect of vanilloid analogs on [$^3$H]RTX binding to the hVR1 receptor at pH 7.4 and pH 8.6. Membranes were incubated with [$^3$H]RTX (0.4 nM) and varying concentrations of vanilloid analogs at 37° C. for 60 min. The data are representative of two experiments with each point assayed in duplicate. The results demonstrate that vanilloid analogs used in this study dose-dependently inhibited [$^3$H]RTX binding at both pH 7.4 (FIG. 3A) and pH 8.6 (FIG. 3B). The $EC_{50}$ values of RTX and capsaicin were slightly decreased from pH 7.4 to pH 8.6. In contrast, the $EC_{50}$ value of capsazepine was significantly increased.
Figure 3B:
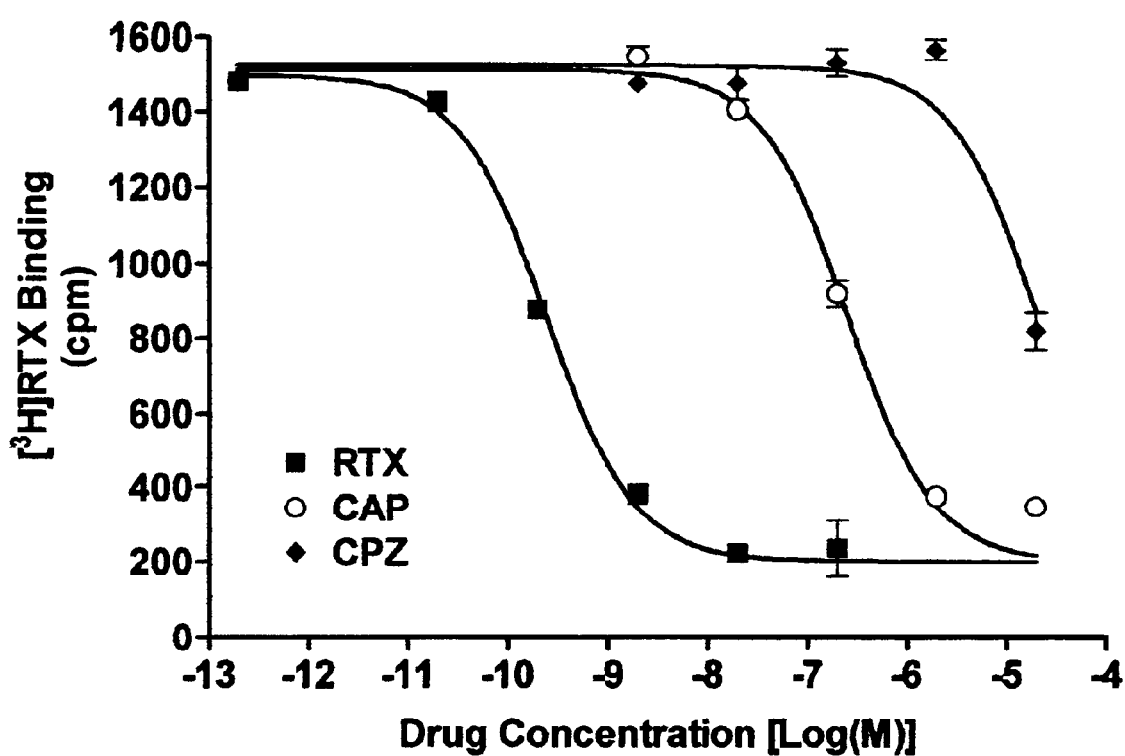

Effect of pH on vanilloid ligand binding to hVR1 receptors. A number of vanilloid ligands were tested for their ability to inhibit the binding of [$^3$H]RTX to hVR1 receptors in pH 7.4 and pH 8.6 buffer. In pH 7.4 buffer, competition for [$^3$H]RTX was in the order: RTX>>capsaicin=capsazepine (FIG. 3a). Similarly, in pH 8.6 buffer, competition for [$^3$H]RTX was in the order: RTX>>capsaicin>capsazepine (FIG. 3b). The $IC_{50}$ values of RTX and capsaicin were slightly decreased from pH 7.4 to pH 8.6 (Table 2). The $IC_{50}$ value of capsazepine was significantly increased from pH 7.4 to pH 8.6 (Table 2). A yellow color is seen in membrane pellets from capsazepine at pH 8.6, suggesting that capsazepine might be oxidized from its double phenol structure to a double quinol structure.

TABLE 2

$IC_{50}$ values of vanilloid analogs which inhibit [$^3$H]RTX binding to hVR1 receptor in buffers with different pH value.

| Buffer | $IC_{50}$ (nM) | | |
|---|---|---|---|
| PH | Resiniferatoxin | Capsaicin | Capsazepine |
| PH 7.4 | 0.78 ± 0.15 | 630 ± 202 | 206 ± 43 |
| PH 8.6 | 0.25 ± 0.03 | 256 ± 37 | >10,000 |

$IC_{50}$ values were obtained from FIG. 3.

Figure 4:
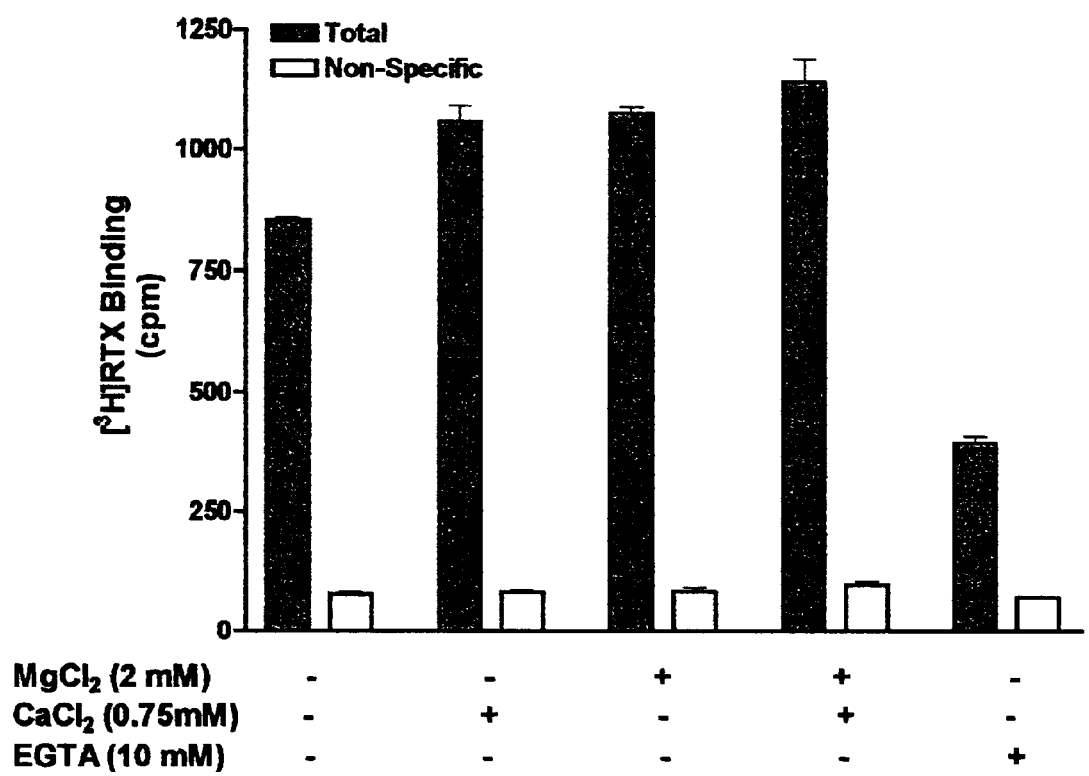
FIG. 4. Calcium and magnesium increased [$^3$H]RTX binding. Membranes were incubated with [$^3$H]RTX (0.25 nM) at pH 8. Without calcium and magnesium the signal was decreased by 20%. EGTA (10 mM) inhibited [$^3$H]RTX binding by 70%.

Effect of calcium and magnesium on [$^3$H]RTX binding. The addition of calcium and magnesium to the assay were found to increase binding and were used to further optimize the assay. The binding assay was performed as described earlier using pH8.0 buffer with the inclusion or chelation of divalent cations. As seen in FIG. 4, the presence of either 0.75 mM $CaCl_2$ or 2 mM $MgCl_2$ increased the total ligand binding compared with the buffer lacking the divalent cations without increasing the nonspecific ligand binding. The presence of both cations increased the ligand binding. In contrast, the presence of a divalent cation chelator, EGTA, reduced the total amount of ligand binding.

There will be various modifications, improvements, and applications of the disclosed invention that will be apparent to those skilled in the art, and the present disclosure is intended to cover such embodiments. Although the present invention has been described in the context of certain preferred embodiments, it is intended that the full scope of the disclosure be measured by reference to the following claims.

References

Acs, G., Palkovits, M., and Blumberg, P. M. (1994). [3H] Resiniferatoxin binding by the human vanilloid (capsaicin) receptor. *Mol. Brain Res.* 23, 185–90.

Bevan, S., Hothi, S., Hughes, G., James, I. F., Rang, H. P., Shah, K., Walpole, C. S. J., and Yeats, J. C. (1992). Capsazepine: a competitive antagonist of the sensory neuron excitant capsaicin. *Br. J. Pharmacol.* 107, 544–52.

Bevan, S., and Szolcsanyi, J. (1990). Sensory neuron-specific actions of capsaicin: mechanisms and applications. *Trends Pharmacol. Sci.* 11, 330–3.

Caterina, M. J., Schumacher, M. A., Tominaga, M., Rosen, T. A., Levine, J. D., and Julius, D. (1997). The capsaicin receptor: a heat-activated ion channel in the pain pathway. *Nature (London)* 389, 816–824.

Szallasi, A. and Blumberg, P. M. (1990). Specific binding of resiniferatoxin, an ultrapotent capsaicin analog, by dorsal root ganglia membranes. *Brain Res.* 524, 106–111.

Szallasi, A. and Blumberg, P. M. (1993). [3H]resiniferatoxin binding by the vanilloid receptor: specific-related differences, effect of temperature and sulfhydryl reagents. *Naunyn-Schmiedeberg's Arch. Pharmacol.* 347, 84–91.

Szallasi, A. and Blumberg, P. M. (1995). Proton inhibition of [3H]resiniferatoxin binding to vanilloid (capsaicin) receptors in rat spinal cord. *Eur. J. Pharmacol.* 289, 181–187.

Szallasi, A. and Goso, C. (1994). Characterization by [3H] resiniferatoxin binding of a human vanilloid (capsaicin) receptor in post-mortem spinal cord. *Neurosci. Letters* 165, 101–104.

Szallasi, A., Goso, C., Blumberg, P. M., and Manzini, S. (1993). Competitive inhibition by capsazepine of [3H] resiniferatoxin binding to central (spinal cord and dorsal root ganglia) and peripheral (urinary bladder and airways) vanilloid (capsaicin) receptors in the rat. *J. Pharmacol. Exp. Ther.* 267, 728–33.

Szallasi, A., Nilsson, S., Farkas-Szallasi, T., Blumberg, P. M., Hoekfelt, T., and Lundberg, J. M. (1995). Vanilloid (capsaicin) receptors in the rat: distribution in the brain, regional differences in the spinal cord, axonal transport to the periphery, and depletion by systemic vanilloid treatment. *Brain Res.* 703, 175–83.

Szolcsanyi, J. (1993). Actions of capsaicin on sensory receptors. In Capsaicin Study Pain, J. N. Wood, ed.: Academic, London, UK), pp.1–26.

Szolcsanyi, J. (1996). Capsaicin-sensitive sensory nerve terminals with local and systemic efferent functions: facts and scopes of an unorthodox neuroregulatory mechanism. *Prog. Brain Res.* 113, 343–359.

Szolcsanyi, J., Szallasi, A., Szallasi, Z., Joo, F., and Blumberg, P. M. (1991). Resiniferatoxin. An ultrapotent neurotoxin of capsaicin-sensitive primary afferent neurons. *Ann. N.Y. Acad. Sci.* 632, 473–5.

Tominaga, M., Caterina, M. J., Malmberg, A. B., Rosen, T. A., Gilbert, H., Skinner, K., Raumann, B., Basbaum, A. I., and Julius, D. (1998). The cloned capsaicin receptor integrates multiple pain-producing stimuli. *Neuron* 21, 531–543.

Wall, P. D., and Melzack, R. (1994). Textbook of Pain (New York: Churchill Livingstone).

Wood, J. N., Winter, J., James, I. F., Rang, H. P., Yeats, J., and Bevan, S. (1988). Capsaicin-induced ion fluxes in dorsal root ganglion cells in culture. *J. Neurosci.* 8, 3208–20.

What is claimed is:

1. A method for measuring ligand binding to a vanilloid receptor comprising the steps of:
   (a) fanning in an aqueous solution having a pH in the range of about 8.0 to about 10.0 a liquid composition comprising a test compound, a labeled ligand, and a human VR1 vanilloid receptor protein;
   (b) incubating the solution for a time sufficient to permit the test compound and labeled ligand to contact the vanilloid receptor;
   (c) measuring the amount of labeled ligand bound to the vanilloid receptor protein; and
   (d) determining if the test compound binds to the vanilloid receptor protein by observing a reduction in the amount of labeled ligand bound to the vanilloid receptor protein, as compared with an equivalent aqueous solution comprising the labeled ligand and the vanilloid receptor protein, but not the test compound.

2. The method of claim 1 wherein the pH is in the range of about pH 8.1 to about 9.1.

3. The method of claim 1 wherein the labeled ligand is a radiolabeled ligand.

4. The method of claim 3 wherein the radiolabeled ligand is tritiated resiniferatoxin.

5. The method of claim 1 additionally comprising the steps after the incubating step of:
   removing unbound labeled ligand from the solution; and isolating the receptor protein.

6. The method of claim 1 wherein the aqueous buffer further comprises a divalent cation selected from the group consisting of:
   (a) magnesium at a final concentration of between about 1 to about 5 mM; and
   (b) calcium at a final concentration of about 0.1 mM to about 2 mM.

7. The method of claim 6 wherein the magnesium concentration is about 2 mM.

8. The method of claim 6 wherein the calcium concentration is about 0.8 mM.

9. The method of claim 5 wherein the removing step comprises adding a sufficient quantity of alpha 1 acid glycoprotein to the aqueous solution to adsorb unbound labeled ligand.

10. The method of claim 1 wherein the steps are performed in order.

11. The method of claim 5 wherein the removing step is performed before the isolating step.

12. A method to measure ligand binding to a vanilloid receptor comprising the steps, in order
   (a) combining in an aqueous solution having a pH in the range of about 8.0 to about 10.0, a test compound, a labeled ligand, and a human VR1 vanilloid receptor protein, said protein being associated with a portion of a cell membrane;
   (b) incubating the solution for sufficient time for the test compound and ligand to contact the vanilloid receptor protein;
   (c) adding a sufficient quantity of alpha 1 acid glycoprotein to the solution to adsorb unbound labeled ligand;
   (d) isolating the membrane from the aqueous solution;
   (e) measuring the amount of labeled ligand bound to the vanilloid receptor protein in the membrane; and
   (f) determining if the test compound binds to the vanilloid receptor protein by observing a reduction in the amount of labeled ligand bound to the vanilloid receptor protein, as compared with an equivalent aqueous solution comprising the labeled ligand and the vanilloid receptor protein, but not the test compound.

13. A method to measure compound binding to a vanilloid receptor comprising the steps, in order, of:
   (a) combining in an aqueous solution having a pH of about 8.6, a test compound, a radiolabeled resiniferatoxin, and a human VR1 vanilloid receptor protein, said protein being a portion of a cell membrane;
   (b) incubating the solution for sufficient time for the test compound and the resiniferatoxin to contact the vanilloid receptor protein;
   (c) adding a sufficient quantity of alpha 1 acid glycoprotein to the solution to adsorb unbound resiniferatoxin;
   (d) isolating the membrane from the aqueous solution;
   (e) measuring the amount of resiniferatoxin bound to the vanilloid receptor protein in the membrane; and
   (f) determining if the test compound binds the vanilloid receptor protein by observing a reduction in the amount of resiniferatoxin bound to the vanilloid receptor protein, as compared with an equivalent aqueous solution comprising the resiniferatoxin and the vanilloid receptor protein, but not the test compound.

14. The method of claim 13 wherein the buffer also contains a divalent cation selected from the group consisting of:
   (a) magnesium at a final concentration of about 2 mM; and
   (b) calcium at a final concentration of about 0.8 mM.

* * * * *